United States Patent [19]

Crosby et al.

[11] 4,285,778

[45] Aug. 25, 1981

[54] PROCESS FOR THE MANUFACTURE OF HALOGENATED HYDROCARBONS

[75] Inventors: John Crosby, Altrincham; Bernard W. H. Terry, Manchester, both of England

[73] Assignee: Imperial Chemical Industries Limited, London, England

[21] Appl. No.: 149,987

[22] Filed: May 15, 1980

[30] Foreign Application Priority Data

Jul. 13, 1979 [GB] United Kingdom ............... 24523/79

[51] Int. Cl.$^3$ ............................................... B01D 3/10
[52] U.S. Cl. ..................................... 203/48; 203/79; 203/80; 203/85; 203/91; 203/95; 570/135
[58] Field of Search ............. 260/653.3, 653.5, 652 P; 203/47, 48, 71, 73, 76, 77, 79, 80, 83, 85, 91, 92, 95, 96

[56] References Cited

U.S. PATENT DOCUMENTS

| | | | |
|---|---|---|---|
| 2,996,527 | 8/1961 | Krespan | 260/653.3 |
| 3,067,264 | 12/1962 | Paciorek et al. | 260/653.3 |
| 3,317,618 | 5/1967 | Hazeldine | 260/653.3 |
| 3,925,491 | 12/1975 | Riess et al. | 260/653.3 |
| 4,210,611 | 7/1980 | Crosby et al. | 260/653.3 |

*Primary Examiner*—Frank Sever
*Attorney, Agent, or Firm*—Cushman, Darby & Cushman

[57] ABSTRACT

2,2-Dichloro-5-methyl-1,1,1-trifluorohex-4-ene, an intermediate in the synthesis of pyrethroid insecticides, is obtained by continuous distillation, preferably under sub-atmospheric pressure, of a mixture of 5-methyl-2,2,4-trichloro-1,1,1-trifluorohexane, dimethylformamide and lithium bromide, precipitating the chlorofluorocarbons from the distillate with water and separating the desired product from starting material by a further distillation.

7 Claims, No Drawings

PROCESS FOR THE MANUFACTURE OF HALOGENATED HYDROCARBONS

This invention relates to a process for the manufacture of halogenated hydrocarbons useful as intermediates in the synthesis of pyrethroid insecticides.

Compounds having the formulae (I) and (II) below:

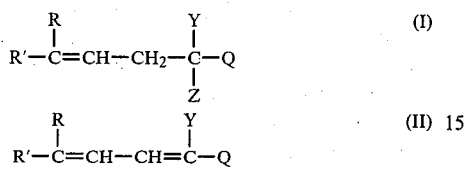

wherein
Y represents a fluorine, chlorine or bromine atom,
R represents a hydrogen atom or lower alkyl group,
R' represents a lower alkyl group,
Z is Y or Q and
Q is $W(CF_2)_m$ in which M is hydrogen, fluorine or chlorine and m is 1 or 2, may be obtained by heating a compound having the formula:

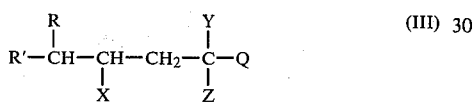

wherein R, R', Y, Z and Q have the previously defined meanings and X represents chlorine, bromine or iodine, provided that X is always bromine or iodine when at least one of Y and Z is bromine, in a polar aprotic solvent, preferably in the presence of an alkali metal halide.

The polar aprotic solvent may be, for example, dimethylacetamide, diethylformamide, hexamethylphosphoramide and dimethylformamide.

The alkali metal halide may be, for example, a fluoride, chloride, bromide or iodide of lithium, sodium or potassium.

The above process is more fully described in our copending United Kingdom Patent Application of earlier date, No. 7924523, filed 13 July 79.

However, under the conditions of this process the compound of formula (I) is liable to undergo further dehydrohalogenation to the compound of formula (II) at a rate which is not very much slower than the initial rate of formation of (I). Consequently, accumulation and separation of (I) may be difficult, requiring techniques such as high performance distillation or preparative scale gas-liquid chromatography (GLC). A typical compound of formula (I) is

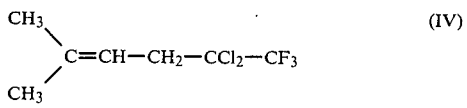

and a typical compound of formula (II) is

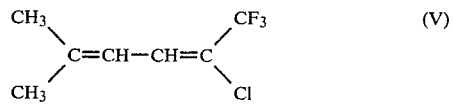

Both of these compounds are valuable intermediates for the synthesis of pyrethroid insecticides. Thus for example (V) may be reacted with a diazoacetic ester $N_2CH.COOR^2$, in which $R_2$ is an alkyl group, in the presence of a suitable catalyst, to give a cyclopropane derivative of formula:

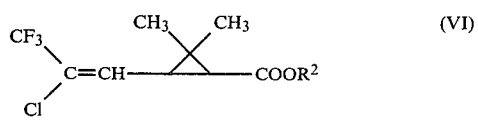

This latter compound may be converted by conventional methods of organic chemistry into a compound of the formula:

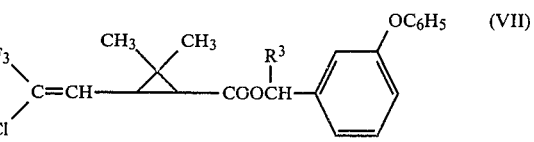

in which $R^3$ is hydrogen, CN or $—C\equiv CH$. Compounds of formula (VII) are powerful insecticides.

Similarly, the compound of formula (IV) may be reacted with diazoacetic ester in the presence of a catalyst to give the cyclopropane derivative of formula:

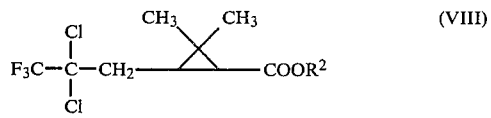

which may then be dehydrochlorinated to give the compound of formula (VI), the subsequent conversion of which into an insecticidal compound of formula (VII) may be carried out as before. This process for the preparation of compounds of formula (VIII), and catalysts for use in the said process, are more fully described in copending United Kingdom patent applications.

The route to compounds of formula (VI) starting from a monoene of formula (IV), although it involves an extra stage compared with the more direct route starting from a diene of formula (V) has the advantage over the latter that formation of the cis IR isomer of the intermediate cyclopropane derivative (VIII) can be favoured when a suitable chiral catalyst is employed in its preparation. This favourable isomer content is carried through into the derived insecticidal compound of formula (VII) and is highly desirable, since it is the cis IR isomer of (VII) which has the greatest insecticidal potency.

A process which enables the monoene of formula (IV) to be prepared essentially free from diene of formula (V) and other by-products is consequently also desirable.

According to the present invention there is provided a process for the manufacture of 2,2-dichloro-5-methyl-1,1,1-trifluorohex-4-ene which comprises continuously distilling a mixture of 5-methyl-2,2,4-trichloro-1,1,1-trifluorohexane, dimethylformamide and lithium bromide, collecting the distillate comprising dimethylformamide, 5-methyl-2,2,4-trichloro-1,1,1-trifluorohexane, 2,2-dichloro-5-methyl-1,1,1-trifluorohex-4-ene and hydrohalide salts of dimethylamine, precipitating the chlorofluorocarbons from the distillate by addition of water and isolating the 2,2-dichloro-5-methyl-1,1,1-trifluorohex-4-ene from the chlorofluorocarbon mixture by distillation.

The first distillation step is preferably carried out under sub-atmospheric pressure in order to minimise by-product formation.

The pressure at which the first distillation step is carried out may be for example from 1000 to 10 mm Hg.

The amount of dimethylformamide which is used may be for example from 100 to 5 moles, conveniently 20 to 8 moles, per mole of 5-methyl-2,2,4-trichloro-1,1,1-trifluorohexane.

The amount of lithium bromide which is used may for example be from 0.1 to 10 moles, conveniently 1 to 5 moles, per mole of 5-methyl-2,2,4-trichloro-1,1,1-trifluorohexane.

The quantity of water which is used to precipitate the chlorofluorocarbons from the distillate is not critical and is conveniently one half of the volume of the distillate.

The 2,2-dichloro-5-methyl-1,1,1-trifluorohex-4-ene prepared by the process of the present invention is of good purity and GLC analysis indicates that typically it may be produced with not more than 5% of isomeric mono-olefins.

The lithium bromide which is an essential, and relatively expensive, feature of the present process is largely retained in the reaction vessel, essentially free from interfering by-products, and may be re-used simply by adding to it appropriate amounts of 5-methyl-2,2,4-trichloro-1,1,1-trifluorohexane and dimethylformamide and carrying out the distillation procedure described above.

The 5-methyl-2,2,4-trichloro-1,1,1-trifluorohexane which is the starting material in the process according to the present invention may be prepared by suitable classical processes of organic chemistry. However, an especially useful process comprises reacting 1,1,1-trichloro-2,2,2-trifluoroethane with 3-methylbut-1-ene in the presence of an amine using a metal halide as catalyst, for example, following the procedure described by Burton et al in Tetrahedron Letters, No. 42, pages 5163-5168 (1966), Pergamon Press Limited.

The following is a typical preparation:

A mixture containing 1,1,1-trichloro-2,2,2-trifluoroethane (37.5 g), 3-methylbut-1-ene (7.0 g), copper (I) chloride (0.1 g) and monoethanolamine (3.05 g) in tertiary butyl alcohol (100 ml) was placed in a glass-lined stainless steel autoclave. The mixture was maintained at 80° C. for approximately 29 hours, with constant stirring.

The resulting brown solution was distilled at atmospheric pressure to remove the alcohol and the remaining solution was distilled under reduced pressure (0.5-0.6 mm Hg). The fraction boiling at 40° C. was collected. The yield of 5-methyl-2,2,4-trichloro-1,1,1-trifluorohexane was 20.6 g (80%), structure confirmed by NMR spectroscopy, and mass spectrographic and elementary analysis.

The invention is illustrated by the following Examples.

EXAMPLES

The following general procedure was used.

Anhydrous lithium halide and dimethylformamide (DMF) are mixed under nitrogen in a round bottom flask equipped with a dropping funnel, stirrer, internal thermometer and distillation column (46 cm×2.5 cm packed with Fenske helices). The reaction vessel is heated in an oil bath and charged with 5-methyl-2,2,4-trichloro-1,1,1-trifluorohexane (A) from the dropping funnel either slowly over a period of several hours or as a single charge at the start of the reaction.

The reaction mixture is then distilled (generally over a period of 2-8 hours) either at atmospheric or subatmospheric pressure. Because carbon monoxide is a by-product of the reaction, the distillation is carried out in a well ventilated fume cupboard.

The crude distillate is diluted with water to precipitate a mixture which comprises mainly unreacted starting material (A), the desired 2,2-dichloro-5-methyl-1,1,1-trifluorohex-4-ene (B) and 2-chloro-5-methyl-1,1,1-trifluorohexa-2,4-diene (C).

After further washing with water to remove traces of DMF the product is dried over anhydrous sodium sulphate any analysed by 'H nmr spectroscopy. If required, B plus C may readily be separated from unreacted A by a simple fractional distillation.

The details and results of Examples 1 to 9 are given in the following Table 1;

TABLE 1

| Ex. | LiBr | LiCl | DMF | (A) | Pressure (mm Hg) | Oil bath temp. (°C.) | Internal temp. (°C.) | Still Head temp. (°C.) | Molar Proportions in the Distillate (A):(B):(C)$^{(a)}$ |
|---|---|---|---|---|---|---|---|---|---|
| 1 | 60g | | 200ml | 50g$^{(c)}$ | 760 | 156-162 | 147-152 | 58-82 | 1:15 |
| 2 | 60g | | 200ml | 50g$^{(d)}$ | 760 | 160-166 | 150-161 | 52-133 | 1:11 |
| 3$^{(b)}$ | | 25g | 200ml | 50g$^{(e)}$ | 760 | 159-162 | 148-152 | 58-92 | 60:40 |
| 4$^{(b)}$ | | 25g | 200ml | 50g$^{(f)}$ | 445 | 131-140 | 128 | 78-92 | 42:48:10 |
| 5 | 25g | | 200ml | 50g | 445 | 138-141 | 128-132 | 85-95 | 45:55 |
| 6 | 25g | | 200ml | 60g | 258 | 132-133 | 123 | 96-101 | 44:56 |
| 7 | 25g | | 200ml | 150g | 220 | 136 | 124 | 104-112 | 55:45 |
| 8 | 25g | | 200ml | 150g | 260 | 136-138 | 117 | 106-111 | 60:40 |
| 9 | 50g | | 200ml | 150g | 280 | 140 | 123-128 | 109 | 68:28 |

NOTES:
$^{(a)}$as determined by 'Hnmr;
$^{(b)}$comparative experiments, not examples of the invention;
$^{(c)}$added dropwise during 1.5 hrs;
$^{(d)}$added dropwise during 1.75 hrs;
$^{(e)}$added dropwise during 3 hrs;
$^{(f)}$added dropwise during 4 hrs.

EXAMPLE 10

The same equipment as used in Examples 1–9 is used in this Example.

The reaction flask is charged initially with lithium bromide (150 g), DMF (600 ml) and 5-methyl-2,2,4-trichloro-1,1,1-trifluorohexane (A) (150 g). The flask is heated in an oil-bath at 140° C. and a vacuum of 240 mm Hg is applied (internal temperature ca. 120° C.). Distillation gives a product consisting essentially of (A), the desired 2,2-dichloro-5-methyl-1,1,1-trifluorohex-4-ene (B), DMF and dimethylamine salts (identified by conversion into N,N-dimethyl-2,4-dinitroaniline). An amount of water equal to approximately one half of the volume of crude distillate is added to the latter and the lower layer, which consists mainly of (A) and (B) with a small amount of DMF, is run off, dried over anhydrous sodium sulphate and analysed by $^1$Hnmr spectroscopy.

After each distillation period the reaction vessel is recharged with sufficient (A) and DMF to give the original composition and the distillation process is repeated. In this way a six cycle preparation was carried out, the results of which are given in Table 2 below:

TABLE 2

| Distillation | Composition of Product | | |
|---|---|---|---|
| | (A) | (B) | DMF |
| 1st and 2nd | 115g | 111g | 0g |
| 3rd | 43g | 48g | 1g |
| 4th | 49g | 39g | 2g |
| 5th | 53g | 33g | 2g |
| 6th | 53g | 32g | 3g |

The material in the still is 'flashed out' by reducing the pressure at the end of the 6th distillation, this comprises only (A) and DMF. The total amount of (A) employed is 718 g. The combined crude distillates are washed with water to remove residual DMF, dried, and then fractioned to isolate (B) (b.p. 89° C./125 mm Hg) and recover (A) for re-use (b.p. 118° C./125 mm Hg).

EXAMPLE 11

Dry dimethylformamide (3 l.), anhydrous lithium bromide (750 g.) and 5-methyl-2,2,4-trichloro-1,1,1-trifluorohexane (750 g.) are charged to a 5 l. reaction vessel fitted with a nitrogen inlet, internal thermometer and a 112 cm × 5 cm (internal diameter) Fenske-packed distillation column with a magnetic reflux divider.

The mixture is distilled during a period of 5 hours with a head temperature of 120–124° C. (temperature of reaction vessel contents ca. 140° C. initially; pressure 385 mm Hg; reflux ratio 15:1). The distillate (1200 ml.) is diluted with water (1 l.) and the lower organic layer (660 g.) is separated, washed with water (2×500 ml.), dried over anhydrous sodium sulphate and distilled at 125 mm Hg pressure to give 2,2-dichloro-5-methyl-1,1,1-trifluorohex-4-ene (480 g.) and unchanged starting material (123 g.). The purity of the monoene, as shown by GLC/nmr analysis, is ca. 90–95%.

We claim:

1. A process for the manufacture of 2,2-dichloro-5-methyl-1,1,1-trifluorohex-4-ene which comprises continuously distilling a mixture of 5-methyl-2,2,4-trichloro-1,1,1-trifluorohexane, dimethylformamide and lithium bromide, collecting a distillate comprising dimethylformamide, 5-methyl-2,2,4-trichloro-1,1,1-trifluorohexane, 2,2-dichloro-5-methyl-1,1,1-trifluorohex-4-ene and hydrohalide salts of dimethylene, precipitating the chlorofluorocarbons from the distillate by adding water to the distillate and isolating the 2,2-dichloro-5-methyl-1,1,1-trifluorohex-4-ene from the precipitated chlorofluorocarbon mixture by distilling said mixture.

2. A process as claimed in claim 1 wherein the first distillation step is carried out under sub-atmospheric pressure.

3. A process as claimed in claim 1 wherein the amount of dimethylformamide which is used is from 100 to 5 moles per mole of 5-methyl-2,2,4-trichloro-1,1,1-trifluorohexane.

4. A process as claimed in claim 3 wherein the amount of dimethylformamide which is used is from 20 to 8 moles per mole of 5-methyl-2,2,4-trichloro-1,1,1-trifluorohexane.

5. A process as claimed in claim 1 wherein the amount of lithium bromide which is used is from 0.1 to 10 moles per mole of 5-methyl-2,2,4-trichloro-1,1,1-trifluorohexane.

6. A process as claimed in claim 5 wherein the amount of lithium bromide which is used is from 1 to 5 moles per mole of 5-methyl-2,2,4-trichloro-1,1,1-trifluorohexane.

7. A process as claimed in claim 1 wherein the amount of water which is used to precipitate the chlorofluorocarbons from the distillate is one half of the volume of the distillate.

* * * * *